United States Patent [19]
Robinson

[11] Patent Number: 6,050,819
[45] Date of Patent: Apr. 18, 2000

[54] DENTAL IMPLANT DISTRACTOR METHOD AND APPARATUS

[75] Inventor: Randolph C. Robinson, Aurora, Colo.

[73] Assignee: Inter-OS Technologies L.L.C., Aurora, Colo.

[21] Appl. No.: 09/119,902

[22] Filed: Jul. 21, 1998

[51] Int. Cl.$^7$ .................................................. A61C 8/00
[52] U.S. Cl. ............................................. 433/173; 623/16
[58] Field of Search .................................. 433/172, 173, 433/174, 175, 176, 201.1; 623/11, 16, 23

[56] References Cited

U.S. PATENT DOCUMENTS

| | | |
|---|---|---|
| 4,011,602 | 3/1977 | Rybicki et al. . |
| 4,744,853 | 5/1988 | Ross . |
| 4,886,456 | 12/1989 | Ross . |
| 4,906,191 | 3/1990 | Söderberg . |
| 5,320,529 | 6/1994 | Pompa . |
| 5,364,396 | 11/1994 | Robinson et al. . |
| 5,489,210 | 2/1996 | Hanosh . |
| 5,584,695 | 12/1996 | Lal Sachdeva et al. ................ 433/173 |
| 5,611,688 | 3/1997 | Hanosh . |
| 5,682,951 | 11/1997 | Linkow . |
| 5,725,377 | 3/1998 | Lemler et al. . |
| 5,769,630 | 6/1998 | Hoffman ............................. 433/173 X |
| 5,899,696 | 5/1999 | Shimoda ................................ 433/173 |
| 5,899,940 | 5/1999 | Carchidi et al. .......................... 623/16 |

FOREIGN PATENT DOCUMENTS

| | | |
|---|---|---|
| 0 791 337 A1 | 8/1997 | European Pat. Off. . |
| 0 832 613 A1 | 4/1998 | European Pat. Off. . |
| WO 98/09577 | 3/1998 | WIPO . |

*Primary Examiner*—Nicholas D. Lucchesi
*Attorney, Agent, or Firm*—Conley, Rose & Tayon, PC

[57] ABSTRACT

Disclosed is an internal mandibular distractor comprising a substantially cylindrical main body, a base, and a shaft. The device is used to gradually separate osteotomized bone sections to promote new bone growth in an area of bone loss. The device is then left in the jaw to also serve as a permanent dental implant for restoring dentition.

83 Claims, 7 Drawing Sheets

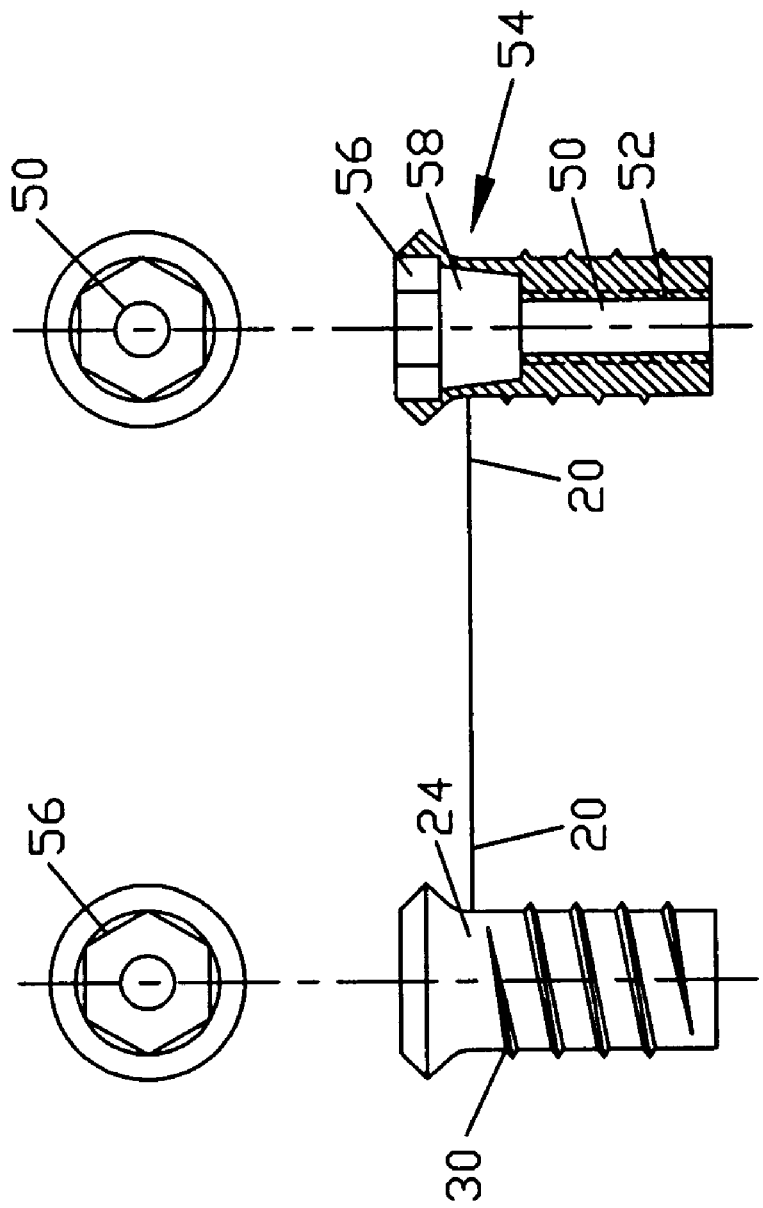

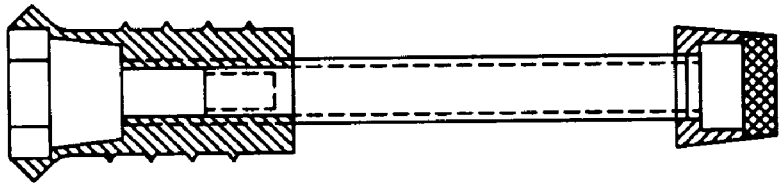
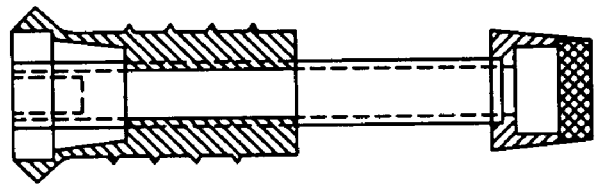
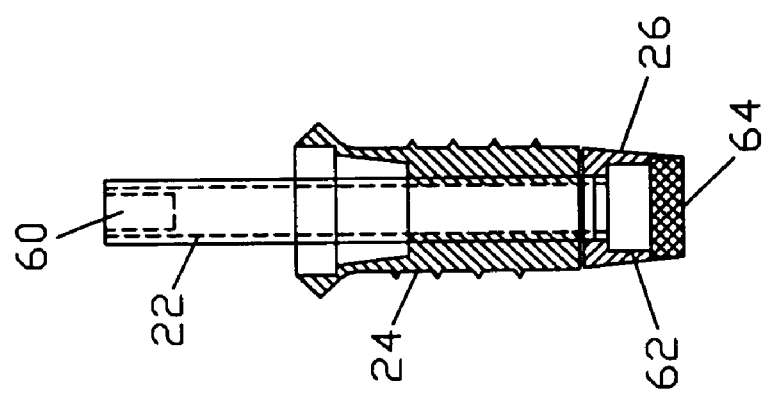
FIG. 5C
FIG. 5B
FIG. 5A

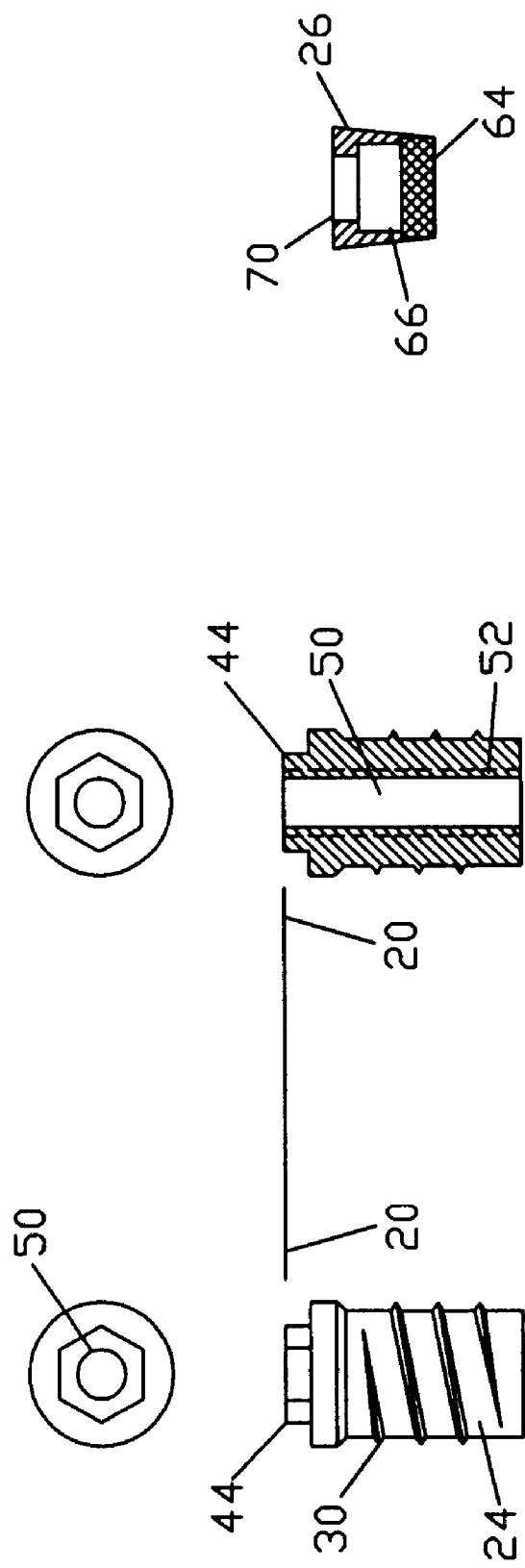

DENTAL IMPLANT DISTRACTOR METHOD AND APPARATUS

BACKGROUND OF THE INVENTION

1. Field of the Invention

The disclosure relates generally to devices designed to distract, or lengthen, bone sections separated by an osteotomy, in addition to serving as a permanent dental implant device. More particularly, the disclosure relates to distraction devices that are internally implantable in an upper or lower jaw, and that are capable of gradual adjustment to distract osteotomically separated bone sections for the purpose of enhancing bone growth. Devices disclosed herein also serve as permanent implants for purposes of restoring dentition.

2. Description of the Relevant Art

The use of dental implants for the replacement of teeth roots and restoration of dentition is known in the art. These devices are typically bullet shaped or screw shaped implants, or anchoring members, with an abutment (post) that extends through the gums and to which the replacement tooth or teeth are attached. The usual practice is to make an incision in the gum to expose the bone, drill a hole in the bone, place an implant in the hole, and then close the gum tissue. The implant is typically left in place for four to six months in order to allow osteointegration, after which the implant is uncovered and a post for rebuilding dentition is placed When there is a deficiency of bone, as occurs when a tooth has been missing for an extended time, for example, then a grafting procedure may be performed with the implant placement, or even four to six months prior to implant placement.

A variety of implant devices have been described. U.S. Pat. No. 4,682,951 to Linkow describes an implant device for use in an area of the maxilla adjacent a descendent portion of the maxillary sinus, particularly in patients with enlarged sinus cavities. This device is anchored in a hole that is predrilled through the bone and into the sinus cavity The anchoring device is a basket or cradle containing bone chips that is inserted into the area of the sinus cavity. The presence of this basket or cradle promotes new bone growth and the device becomes osteointegrated. Posts attached to this basket or cradle then serve as implants for the attachment of artificial teeth.

U.S. Pat. Nos. 4,744,753 and 4,886,456 to Ross and U.S. Pat. No. 4,906,191 to Söderberg describe devices and methods for forming dental prostheses. Prior to producing a model for use in tooth replacement, an implant is placed in the jaw and allowed to integrate. The replacement dentition is modeled, typically using a heat meltable material that forms around a post or screw attached to the implant. This model is then used in the manufacture of a permanent tooth or teeth.

U.S. Pat. Nos. 5,489,210 and 5,611,688 to Hanosh include expandable, bullet-shaped dental implants that are inserted into predrilled holes in the jaw and provide threaded connections for attachment of prostheses. These devices further provide internal threading for insertion of a screw within the device. Activation of this expander screw causes the implant to expand for more secure anchoring in the predrilled hole in the jaw. A dental implant device described in U.S. Pat. No. 5,725,377 includes an internal battery so that a small electrical field generated by the implant stimulates bone growth.

Bone distraction devices are also known in the art. Orthopedic distraction, for example, has been used for several decades. One method of promoting bone growth involves cutting the bone, distracting (separating) the two pieces of the bone a desired distance, setting the two ends in place by means of a bridge across the two bone sections, and filling the gap between the bone ends with a bone segment or graft.

Devices for gradual bone distraction are described in U.S. Pat. No. 4,096,857 to Kramer and U.S. Pat. No. 3,976,060 to Hildebrand. European Patent Application No. EP 0 791 337 to Razdolsky and Driscoll describes a device for lengthening the jaw by stretching the jaw of a young person during growth, a process that can be accomplished without cutting the jaw bone. The device is also described as useful in older patients and more severe cases when used in conjunction with a corticotomy. Several devices that may be attached externally to the jaw have been described for mandibular distraction. Examples of such devices include those described in European Patent Application No. EP 0 832 613, PCT Publication No. WO 98/09577 and U.S. Pat. No. 5,364,396.

There is still a need, however, for devices and methods that allow a practitioner to replace degenerated or otherwise deficient bone, and also to place a permanent implant device to be used for replacement dentition, without requiring separate surgeries for bone replacement and implant placement.

SUMMARY OF THE INVENTION

A distractor/implant device is disclosed herein that may be used to provide gradual distraction between separated bone sections, thus encouraging bone growth between the distracted sections. The device is inserted into a bone segment, such as a jaw bone segment, preferably in conjunction with an osteotomy. In certain embodiments, the jaw may be predrilled with a hole of compatible size and depth for insertion of the device. An osteotomy may then be made just beneath the predrilled hole, such that when the bone segments are separated, the hole will extend into the separation. After insertion of the device, the bone segments are separated or mobilized. The device then gradually distracts (separates) the bone segments, thus encouraging or promoting new bone growth in the space between the separated bone segments. In certain embodiments the gradual separation of bone segments is continued until a certain distance is obtained, thereby restoring bone to an area of bone depletion, degradation, or other deficiency. As such, the device may be used to improve an area or condition of deficiency of bone due to injury, trauma, disease, decay, neglect, genetic defect, or the like.

A distraction device as disclosed herein may also serve as a dental implant. In certain embodiments, a device as described herein may be allowed to osteointegrate, and may thus be effective to provide an implant or anchoring device for a dental abutment or prosthesis. As used herein, "osteointegrate" or "osteointegration" of a device or object have the standard meanings known in the art, and are further defined as a condition or action in which the device or object is left in a living bone for such a time that a portion of bone grows to surround or adhere to the device or object. These terms may also include the meanings that the device or object is tightly held or not easily movable within or relative to the section of bone. In certain embodiments, a device as disclosed herein may serve as a dental implant by providing for the attachment of a dental abutment. A device may be configured to be compatible with standard abutments and dental restoration fixtures known in the art, or it may be configured to be compatible with abutments and restoration fixtures of nonstandard dimensions. Described herein are devices that are compatible with abutments requiring an external hexagonal attachment, an 8° Morse taper configuration, a spline configuration, an internal hexagon, a screw retained abutment, a cement retained abutment, an exterior square post, an exterior octagonal post, an internal square, or an internal octagon, for example. The disclosure of these examples is not intended to be limiting, and other configurations may also be provided.

During use, the devices disclosed herein may provide structure and stability for bone distraction and dentition restoration. In certain embodiments these devices also allow for efficient removal of a temporary abutment and placement of a final abutment for restoration of teeth. The devices may be made of any biocompatible materials of sufficient strength and resilience, including, but not limited to titanium, stainless steel, ceramic, a precious metal, or an alloy or combination of these. In alternative embodiments, the devices may include a coating of a substance such as hydroxylapatite or other minerals, or plasma, for example, or texturing to aid the osteointegration process. Such surfaces may be applied by any method known in the art, such as by dipping, painting, spraying, chemical bonding, electroplating, sand blasting, ball peening, or they may be incorporated into the material from which the device is constructed. In addition, the devices may include roughened or grooved surfaces, patterned grooves such as diamond patterns, holes, depressions, projections, or other texturing on or in the exterior surface. Other materials or techniques known in the art to aid retention of a medical implant in a bone are also contemplated to be applicable to the devices disclosed herein.

In certain embodiments, the distraction devices include a main body, a base, and an elongated member configured to pass through the main body and contact the base during use. During distraction, the main body is held tightly in the upper bone segment and the elongated member is urged through the main body in the direction of the base, which provides a solid platform. The movement of the elongated member thus separates, or distracts the main body (attached to the upper bone segment) from the lower bone segment, which may contact or possibly contain the base. The main body is preferably elongated and may be substantially cylindrical, bullet shaped, polygonal, or other regular or irregular shape. The main body may include an internal channel or duct, or a threaded internal bore configured to allow the elongated member or shaft to extend through the channel and to engage the main body during use. The main body may also provide a top designed to accommodate a dental abutment as described above and the exterior coatings threading and/or other methods of securing the main body in a bone. The top of the main body may also provide a means for driving the device into the bone. This means may also serve as the attachment for an abutment. For example, an external hex may be used to drive the device into the bone and may then also serve as an attachment for an abutment that requires an external hex. Or the means for driving the device into the bone may be a separate structure such as an internal hex, an internal polygon, a slot, or crossed slots. Any configuration may be used so long as it does not interfere with, or block the channel of the main body, so that the shaft can extend above the main body in the pre-distraction position.

The device also includes a base configured to be implanted beneath the main body (distal to the bone crest) in a bone to be distracted. The base may have a proximal surface that is adjacent the main body in the undistracted position, and a distal surface, and the base may be substantially cylindrical, bullet shaped, or tapered inwardly from the proximal to the distal surfaces. The base may also be provided in any shape as described above for the main body. The base may also engage the main body in a way that prevents rotation of the base with respect to the main body. For example, the base may include guide pins or rods that extend from the proximal surface and mate with openings so that the pins are slidable into the main body. Alternatively, the base may include a cylindrical shell that projects from the proximal surface, or the shell may be the outer surface of the base. In either case, the cylinder mates with a complementary opening in the main body so that the two pieces fit together in a telescopic arrangement. A telescopic arrangement, or engaging telescopically, is used herein to mean that one piece slides into the other as is common with the parts of a hand telescope. The base and main body may also include fingers that interdigitate, including fingers and grooves that may be formed on the outer surfaces of the main body and base such that the two bodies are preventing from rotating with respect to each other. Any other means of interaction of the main body and base could also be used, as long as the elongated member is still able to distract the main body away from the base during the distraction process. The interacting means or design may be configured so that the main body and base continue to interact through a part of, or even the entire distraction process, or they may interact only in the pre-distraction position.

The exterior of the base may be smooth, or it may also include any of the surface coatings, threading or textures as described above, either together with or independently of, any threading, texture or coating of the main body. The base may include a cavity, depression, indention, or hole that aligns with the channel or duct of the main body to form a contiguous channel during use. In certain embodiments the base includes a closed ended cavity, ending in a base cap, to provide a solid platform to receive an end of an elongated member. During use, the elongated member may extend through the channel in the main body, into the cavity of the base, and contact the base cap at the bottom of the cavity. Other configurations may also be used, so long as the elongated member can be activated and the end of the member is constrained from passing completely through the base.

The device may further include an elongated member such as a shaft, rod, bar, or the like configured to be disposed within and extend through the internal channel of the main body and into the base. The elongated member provides a means of engaging the main body so that the main body may be controllably urged along the length of the elongated member when the member is activated. The elongated member is also configured to be held in the base such that, during activation, the base provides a solid distraction surface and does not move relative to the length of the elongated member. In certain embodiments, the base includes a cavity with an opening into the cavity through which the elongated member passes. The shaft of the elongated member is smaller in diameter than the opening into the cavity so that the member can freely rotate in the base. In some embodiments the elongated member includes an enlarged end that is configured to be held in the base. In those embodiments, the end of the elongated member may be larger than the opening into the cavity in the base so that the elongated member may not be easily removed from the cavity. In other embodiments, the diameter of the end of the elongated member is smaller than the diameter of the opening into the cavity of the base so that the member may be easily inserted into or removed from the base.

In those embodiments in which activation of the elongated member includes rotating the member, the member may freely rotate in the base, or the base may rotate concurrently with the member so long as the base is immobile with respect to the long axis of the member. In certain embodiments the elongated member may be from about 3 millimeters to about 20 millimeters in length, or longer if needed. The length of the elongated member is determined by a practitioner based on the amount of distraction required. Typically the member is from about 1 to 3 millimeters in diameter, depending on the width of the main body. The elongated member may also include an activation device, effective during activation to distract the main body from the base of the device. The activation device may include, but is not limited to a hexagonal head or cavity, a square head or cavity, a polygonal head or cavity, a slot, or a crossed slot. The activation device may be any effective conformation that allows activation to continue during the latter stages of distraction when the top of the elongated member is contained in the duct of the main body. The device may also include, in certain embodiments, an activation tool, such as a wrench or driver to interact with the activation device.

In certain embodiments the internal channel of the main body is threaded and the elongated member is threaded to engage the threads in the channel. In those embodiments, activation includes rotating the elongated member so that the main body is threadably advanced along the elongated member, which may freely rotate in the base. The internal threading near the top of the main body may be configured to accept a threaded dental abutment or prosthesis, or a screw or other threaded member for attaching an abutment. The threading near the top may then serve to engage the elongated member during the distraction process, and then may also serve to engage a threaded abutment after distraction, when the elongated member has moved down into the main body, exposing the top threads. Alternatively, threads at the top of the channel of the main body may be configured to mate with an abutment, but not with the elongated member, which would then pass by the top threads into the channel without engaging the threads at the top of the channel.

Certain distraction devices disclosed herein may serve as dental implants. Such devices are configured such that, after the distraction process is complete, a dental abutment or prosthesis may be attached or affixed to the top of the device. In certain embodiments, therefore, the disclosed devices may include a dental abutment, or a dental abutment attached to the main body. The devices described herein may also include an activating tool or an activating wrench. Such a wrench may include a removable ratchet driver and a handle, or it may be constructed of a single piece that includes a handle and a head for interaction with the device. The head may be a fixed piece or it may be a ratchet. Certain activation wrenches may serve to drive the device into the bone, or they may serve to activate the elongated member during distraction, or they may serve both purposes. Activation wrenches that serve to drive the device into the bone also provide a hole for extension of the elongated member above the device.

In certain embodiments a dental distraction device comprises a main body, a base, and a shaft. The shaft is used to control the relative position of the main body and base during distraction of an osteotomized bone. The device may be left in the bone after distraction as a dental implant. The main body defines a concentric axial channel with internal threading. The shaft comprises complementary threading such that when the two sets of threads are engaged, rotation of the shaft with respect to the main body causes the main body to move along the shaft. In this embodiment, the base defines a cylindrical, close ended support for an end of the shaft, within which the shaft is freely rotatable. In alternative embodiments, the closed end of the close ended support is either a flat surface or a rounded surface.

Described herein are methods of distracting a jaw bone in need thereof. These methods include providing a bone distraction device, as described above; drilling a hole of a size and shape to accommodate the bone distraction device in the bone; making an osteotomy just below the hole; inserting the bone distraction device in the hole; separating the superior osteotomized bone segments and inferior osteotomized bone segments, allowing callus (early bone) to form in the osteotomy; separating the main body and the base by activating the shaft, thus stretching the osteotomy; allowing the bone callus in the osteotomy to grow; and repeating the two previous steps until the desired bone height is reached.

A method of providing a dental implant in an area of vertical bone loss is also described herein. The method includes providing a bone distraction device, as described above; drilling a hole of a size and shape to accommodate the bone distraction device in the bone; making an osteotomy just below the hole; inserting the bone distraction device in the hole; separating the superior osteotomized bone segments and inferior osteotomized bone segments, allowing callus (early bone) to form in the osteotomy; separating the main body and the base by activating the shaft, thus stretching the osteotomy; allowing the bone callus in the osteotomy to grow; repeating the two previous steps until the desired bone height is reached; and allowing the bone distraction device to remain in the distracted bone to serve as a permanent dental implant.

A part of the disclosure is a method of manufacturing a combination bone distraction and dental implant device. In one embodiment, the method comprises providing a main body, wherein the main body may include an internal channel and a top designed to accommodate a dental abutment. The method also includes providing a base designed to abut or to slidably engage the main body in the undistracted position. The base may include an internal cavity configured to align with the internal channel of the main body to form a contiguous channel. The cavity in the base may terminate in a surface configured to accept an end of a shaft and provide a solid distraction platform against which a shaft is freely rotatable.

A shaft is also provided in the method. The shaft or elongated member may range from about 3 millimeters to about 20 millimeters in length. During use, the shaft is disposed within and extending into the internal channel of the main body and the cavity of the base. The shaft may include threads configured to mate with a threaded internal channel of the main body and it may further include an activation device. The activation device may be a hexagonal projection or cavity, a square head or cavity, a polygonal head or cavity, a slot, or a crossed slot.

In a further embodiment of the disclosure, a method of anchoring a dental prosthesis in an area of low bone density is described. This method includes providing a bone distraction device as described herein; making an incision in the gum tissue and exposing the bone of the upper or lower jaw; drilling a hole the diameter of the device and tapping the bone to accommodate the main body; screwing or inserting the devise into position; osteotomizing the jaw bone just below the device; allowing the superior osteotomized bone segments and inferior osteotomized bone segments to partially separate; closing the gingiva; and periodically activating the shaft by means of an activation wrench.

It is understood that the any of the devices or methods described herein in any of their embodiments, although described in the singular, may be duplicated so that a plurality of implants are provided and are activated in uniform or independently as needed. Thus, a larger section of jaw may be distracted by the use of spaced apart distractor/implant devices to provide support for a dental bridge or for a plurality of artificial teeth. Examples of this are illustrated at least in FIGS. 1 and 2.

BRIEF DESCRIPTION OF THE DRAWINGS

The invention will be more readily understood by reference of the accompanying drawings wherein like reference numerals indicate like elements throughout the drawing figures, and in which:

FIG. 4A is a side view and top view of the main body embodying a Morse taper configuration.

FIG. 4B is a cross-sectional view of FIG. 4A.

FIGS. 5A–C are cross-sectional views of an assembly of the disclosure embodying a Morse taper, in a pre-, mid-, and full-distraction position, respectively.

FIG. 6A is a side view and top view of the main body embodying a hex abutment configuration.

FIG. 6B is a cross-sectional view of FIG. 6B.

FIG. 8 is a cross-sectional view of a base.

DETAILED DESCRIPTION OF THE INVENTION

Figure 1:
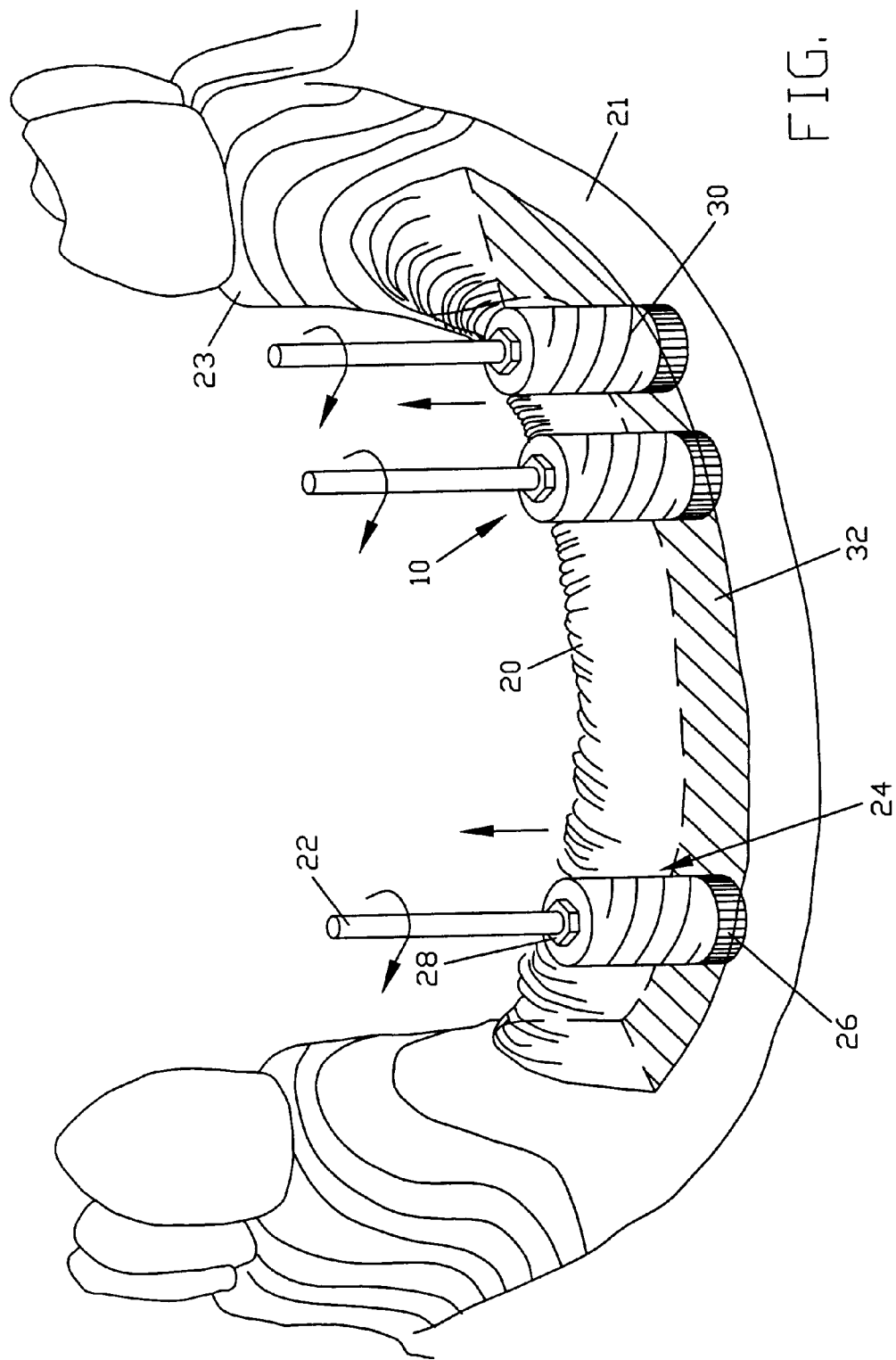
FIG. 1 is perspective view of an embodiment in a pre-distraction phase.

Turning first to FIG. 1, there is shown a distraction/implant device 10 (device) in a pre-distraction phase or position. As shown in this embodiment, the gingiva or gum tissue 23 has been cut to expose the bone 20 of an upper or lower jaw. In the embodiment shown, a hole may have been drilled in the bone 20 to accommodate the insertion of a device 10. The device 10 as shown includes a main body 24, base 26 and an elongated member or shaft 22. In certain methods of use of the device as shown in FIG. 1, the bone is tapped to accommodate external threads 30 that may be provided on the main body 24. External threads may also be present on the base 26. The device 10 is inserted into position in the pre-drilled hole, and in certain embodiments, screwed into the hole using the external threads. As seen in FIG. 1, the device may be implanted to a depth such that the top 28 of the main body is positioned near the crest of the bone 20 and the elongated member 22 extends above the bone. An osteotomy (cut made in the jaw bone) is just below the device 10 to create superior osteotomized bone segments 20 (superior segments) and inferior osteotomized bone segments 21 (inferior segments), which may be separated by a gap 32. During use, after the device is in place, the gingiva (gum tissue) 23 is closed.

While the device 10 is in the pre-distraction position, as shown in FIG. 1, for example, a base 26 is adjacent to and may contact a main body 24 of the device. As shown in FIG. 5A, in the pre-distraction position an elongated member or shaft passes through an opening or internal bore 50 of the main body 24 and extends into the cavity 66 of the base 26. The bottom 62 of the shaft 22 may rest on the base, against the bottom of the cavity, or on base cap 64 to provide a distraction platform. The internal bore 50 preferably includes internal threading 52 that mates with external threading 42 of the shaft 22, so that turning of the shaft 22 with respect to the main body 24, or turning of the main body 24 with respect to the shaft 22 results in displacement of the main body 24 along the shaft 22. Other structures that allow implementation of a controllable, incremental movement of an elongated member 22 through a main body 24 may also be used in certain embodiments. For example, one may use a ratcheting arrangement including one or more notches on the elongated member that interact with a projection or tooth to control the motion, or one may utilize one or projections on an elongated member to interact with one or more slots, for example, included in a main body 24.

Figure 2:
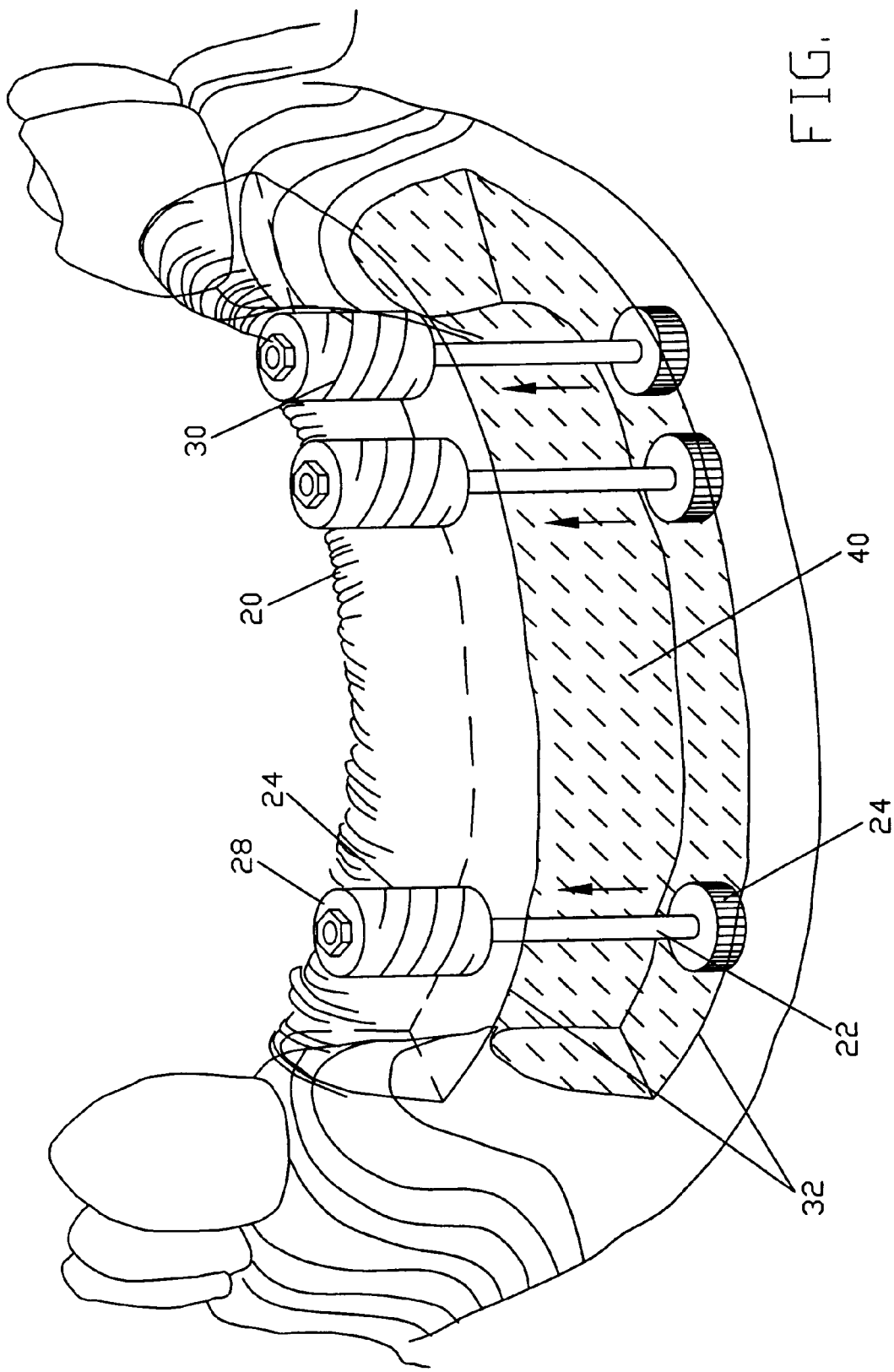
FIG. 2 is a perspective view of an embodiment in a post-distraction phase.

Now turning to FIG. 2, an embodiment of the disclosure is shown in a post-distraction phase. Approximately three to seven days after a device 10 is implanted, or at a time determined by the practitioner to be acceptable to avoid complications, a shaft 22 of the device 10 is activated, or turned, preferably using an activation device 60 (shown in FIG. 3), which is configured to interact with a wrench or other tool. In particular embodiments, an activation device 60 may be a square cavity configured to receive a square head of a wrench or driver. Upon turning the shaft 22 in the appropriate direction, as dictated by the threading in those embodiments employing threading, the shaft is urged by the threading to move through the internal bore 50 of the main body 24. The end of the shaft 62 abuts the base cap 64, which rests in or on the solid bone segment 21, providing a solid resistance for the shaft. Activating the shaft 22, therefore, may move the main body 24 away from the base 26, creating or enlarging a gap 32 between the superior bone segments 20 and the inferior bone segments 21. This action may stretch the bone callus between the superior segments 20 and the inferior segments 21, and encourage generation of new bone (callus) 40. This process may be repeated in small increments until the crest of the bone 20 reaches the desired height and the shaft 22, preferably no longer extends above the main body 24. After distraction, the device may be left in the bone and may be used as a permanent implant.

Figure 3:
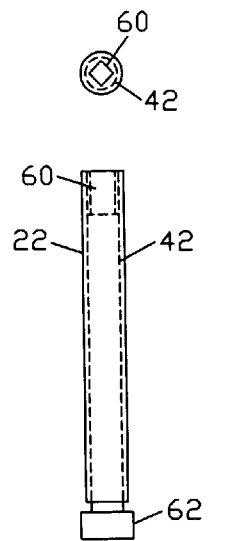
FIG. 3 is a cross-sectional view and top view of a shaft.

In FIG. 3 there is illustrated an elongated member or shaft 22 of a device 10. The shaft 22 may include an activation device 60 external threading 42 and an end or base 62 for interacting with the base cap 64. A top view of a shaft is also shown, depicting an embodiment in which the activation device 60 is a square cavity for receiving a square headed wrench or driver. The length of distraction needed is determined by the practitioner based on the extent of bone loss or deficiency and a shaft 22 of the proper length is chosen for the distraction device. Typical distraction lengths may include any length from about 2 millimeters, up to about 20 millimeters, and would include, of course, any length in between. In certain embodiments, shafts or elongated members may be provided in various lengths, to be selected and used interchangeably as needed. In such a packaging arrangement shafts of from about 5 millimeters to about 8 millimeters to about 11 millimeters to about 15 millimeters or even to about 18 millimeters in length may be included in any combination as a set, for example. It is also understood that a shaft may be shortened as needed by a practitioner or other user by cutting, sawing or grinding, for example. All such modified shafts would also fall within the scope and spirit of the present disclosure.

One example of a device is shown in cross-section in FIGS. 5A–5C, which demonstrate a device 10 in a pre-distraction position (FIG. 5A), a mid-distraction position (FIG. 5B) and a post-distraction position (FIG. 5C). The base 26 and the main body 24 are adjacent in the pre-distraction position, and the shaft 22 extends above the main body 24. As distraction progresses, the main body 24 travels along the shaft 22, moving away from the base 26 as shown in FIG. 5B, until the distraction is complete (FIG. 5C). FIG. 5C shows the main body 24 as having moved along the shaft 22 until only the top of the shaft is contained within the main body 24. Although there is no requirement that the main body 24 move that far, preferably the top of the shaft 22 is far enough down in the internal bore 50 that it does not interfere with any abutment that is to be attached to the top of the implant device.

As discussed above, the main body 24 and the base 26 may be urged apart by the interaction of internal threading 52 of the internal bore 50 of main body 24 and the external threading 42 of the shaft 22 as the shaft 22 is turned by an activation wrench, for example. The cavity 66 of the base 26 holds the shaft end 62 and may allow the shaft 22 to rotate freely against the base cap 64, thus providing a solid distraction platform against which the force of the turning threads may be applied, urging the main body 24 to move along the shaft 22. In certain embodiments the bottom 62 of the shaft 22 may be of a larger diameter than the entrance 70 into the cavity 66 such that the shaft 22 is retained within the base 26, and freely rotates but is not easily removable. Such an arrangement may be helpful to a practitioner in inserting the device. In certain embodiments the entrance 70 may be large enough with respect to the end 62 of the shaft 22 so that the shaft is easily insertable and removable.

In certain preferred embodiments, the device 10 comprises a top 28 that is configured to be compatible with a dentition abutment, so that an abutment or restorative fixture may be attached thereto. The top 28 of a device 10, which may contain a connector for an abutment may be designed to be compatible with an abutment or fixture of any size or shape known in the art. As such, the device 10 may include an external member or projection (male connector) that is configured to mate with a complementary internal shape (female connector) contained in an abutment. Alternatively the device 10 may include an internal cavity or female connector configured to mate with an external or male connector contained on an abutment. The described connectors may be of any appropriate shape and are in many cases hexagonal. Any polygonal shape such as a square, a triangle, a rectangle, an octagon or a dodecagon, for example may also be used. Irregular shapes may also be used, such as a shape that orients the abutment in a particular direction relative to the implant device. Also contemplated are junctions of the device and an abutment in which projections are present on a device and offset projections are also present on the abutment so that the two sets of projections slide past each other during use to form a tight fit. This type of connection may be particularly useful as radial projections in a circular connector.

Typically abutments are attached by a screw or other securing means. In such embodiments, the connector of the abutment has a hole through the center thereof, which may or may not be threaded or provide other appropriate means for securing the connection. In a preferred embodiment, a hole or threaded opening through an abutment connector is alignable with the bore or opening 50 in a device 10 when the connectors are joined to form a contiguous channel for connection of an abutment. Should the opening in the abutment not be threaded, a screw may still be used that is compatible with threading in the internal bore 50 of a device 10. This threading may also be used in the distraction process when the abutment screw and a shaft 22 have the same size and pitch threading. In certain embodiments, a shaft 22 may have a smaller diameter than an abutment screw so that the shaft does not contact the threads in an upper portion of the bore 50. As used herein the term "bore" is meant to describe a structural feature of a device that may be threaded or unthreaded, and the term is not meant to limit the structural feature to any particular method of manufacture or configuration. An opening 50, through a device 10 may be described as a bore, tunnel, channel, hole, opening, passage, duct, conduit, or the like.

FIGS. 4A and 4B depict an embodiment of the disclosure in which a connector 54 of a device is configured to be compatible with an abutment configured in an 8° Morse taper 58, as is well known in the art. Also shown in FIG. 4B is an internal hexagon configuration 56 used for driving or screwing the device into the bone.

Figure 7A:
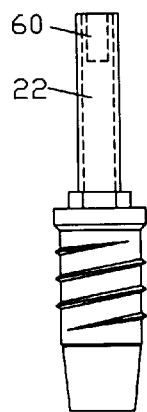
FIGS. 7A–C are perspective views of an assembly of the disclosure embodying a hex abutment concept, in a pre-, mid-, and full-distraction position, respectively.
Figure 7B:
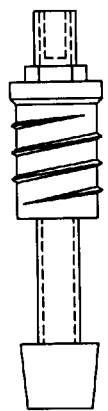
Figure 7C:
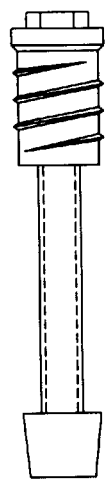
Figure 7D:
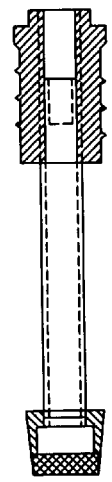
FIG. 7D is a cross-section view of 7C.
Figure 9:
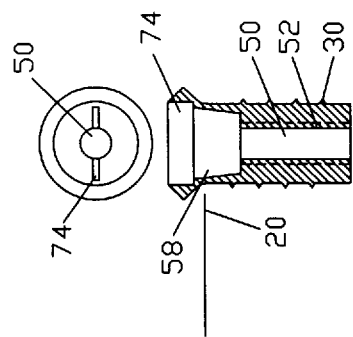
FIG. 9 is a cross sectional view and top view of a device that includes a slot to drive the device into a bone.

FIGS. 6A and 6B depict an embodiment in which another type of standard abutment may be attached to an implant device. This embodiment comprises a top 28 of the main body 24 comprising an external hexagon 44 for attachment of compatible standard abutments known in the art. The hex 44 may also serve to drive or screw the device into the bone. FIGS. 7A–7C depict an external hex embodiment in the pre-distraction, mid-distraction and post-distraction positions, respectively. Other abutment connection mechanisms, such as a spline configuration, an internal hexagon, a screw retained abutment, a cement retained abutment, an exterior square post, an exterior octagonal post, an internal square, an internal octagon, or others that are currently known or may be developed in the future may also be compatible with the implant devices disclosed herein. Appropriate abutment connections may also be used to drive or screw the device into a bone. Configurations for driving the device would also include, but would not be limited to external or internal polygons such as squares, triangles, hexagons, octagons, dodecagons, slots, crossed slots, or star patterns, for example. FIG. 9 depicts an embodiment of the device configured to attach to an abutment with a Morse taper configuration and in which a slot 74 is used to drive the device into bone.

FIG. 8 is a cross-sectional view of a base 26. A base may include a cavity or a closed ended hole 66 in the base 26 and a base cap 64. An opening 70 into the cavity 66 may be narrower than the cavity in order to retain a shaft end 62 within the base, and still allow the shaft to rotate freely against the base cap 64. In such embodiments, the shaft end 62 is smaller in diameter than the cavity 66, but larger in diameter than the opening 70. In certain embodiments the shaft end 62 may pass freely through the opening 70 for easy removal of a shaft 22. The base may be formed or milled from a single piece, or it may be constructed of at least two pieces and welded or otherwise bonded together. The base may provide external threading to facilitate placement of the device in a predrilled hole, or the external sides may be smooth or textured. The exterior of a base may also be coated as described above regarding a main body 24. The internal cavity 66 is configured to align with an internal bore or duct 50 of a main body 24, during use, however the cavity 66 may be of a slightly larger diameter and unthreaded in order to allow the shaft 22 to rotate freely in the cavity 66.

Figure 12:
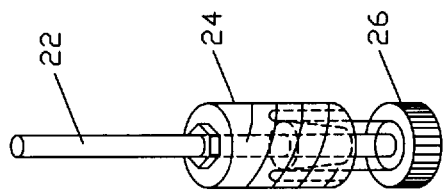
FIG. 12 is a side view of a device in which the base telescopically engages the main body.
Figure 10:
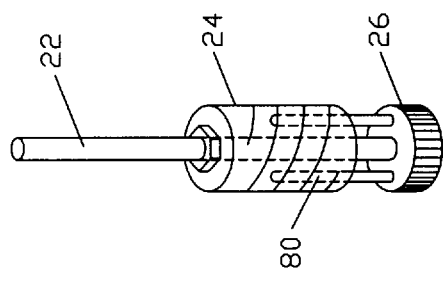
FIG. 10 is a side view of an embodiment in which the base includes pins that engage the main body.
Figure 11:
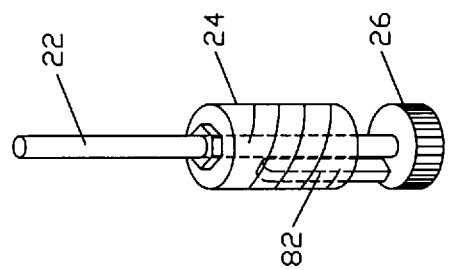
FIG. 11 is a side view of a device in which a finger on the base interdigitates with the exterior surface of the main body.

FIGS. 10–12 show embodiments of the disclosed devices that include various types of interactions between the main body and base. In the embodiment shown in FIG. 10, a plurality of pins 80 extend upward from the proximal surface of the base 26 and slide into holes in the main body 24 when the device is assembled. The device is shown in a slightly distracted position. This arrangement prevents the base from rotating with respect to the main body during activation of the elongated member 22, but does not prevent rotation of the elongated member with respect to the main body or base. FIG. 11 shows an embodiment in which one or more fingers 82 project from the proximal surface of the base 26 and are configured to fit into the same number of grooves on the surface of the main body 24. In this embodiment, as in the pin arrangement, the base is prevented from rotating with respect to the main body during activation of the elongated member 22, but the elongated member is free to rotate with respect to the main body and the base. FIG. 12 shows an embodiment in which the base 26 includes a cylindrical projection that telescopically fits into a groove in the main body 24. The projection may be a complete or partial cylinder. In embodiments that are partially cylindrical, such that a two dimensional projection is one or more arcs rather than a complete circle, the base would again be prevented from rotating with respect to the main body. In the embodiments shown in FIGS. 10–12, an external hex is shown for driving the devices into the bone. It is understood that any means as described herein for driving the device into the bone, and also for attaching an abutment, or any combination of these could be combined with these embodiments.

In the practice of the methods and use of the devices disclosed herein, the device 10 may be left in place after the full distraction has been accomplished to serve as a permanent implant device. Typically, after distraction is complete, a temporary abutment may be attached to the implant for a period of from four to six months and then replaced with a permanent abutment in order to restore dentition.

What is claimed is:

1. A distraction device comprising:
    an elongate main body, wherein the main body comprises:
        an internal duct; and
        a top configured to connect to a dental abutment;
    a base configured to accept an end of an elongated member and provide a distraction platform; and
    an elongated member comprising an activation device and configured to be disposed within the internal duct of the main body and contact the base;
    wherein activation of the elongated member is effective to urge the elongated member through the duct of the main body toward the base during use.
2. The distraction device of claim 1, wherein the main body is substantially cylindrical.
3. The distraction device of claim 1, wherein the internal duct comprises threading and the elongated member comprises threading configured to mate with the threading in the internal duct.
4. The distraction device of claim 1, wherein the internal duct is configured to provide a threaded connection for an abutment.
5. The distraction device of claim 1, wherein the distraction device provides a connection for an abutment requiring an external hexagonal attachment, an 8° Morse taper configuration, a spline configuration, an internal hexagon, a screw retained abutment, a cement retained abutment, an exterior square post, an exterior octagonal post, an internal square, or an internal octagon.
6. The distraction device of claim 1, wherein the top of the main body comprises a male connector for an abutment.
7. The distraction device of claim 1, wherein the top of the main body comprises a hexagonal projection.
8. The distraction device of claim 1, wherein the top of the main body comprises a female connector for an abutment.
9. The distraction device of claim 1, wherein the top of the main body comprises an internal 8° taper connection for an abutment.
10. The distraction device of claim 1, wherein the top of the main body comprises a connector for driving the distraction device into a bone.
11. The distraction device of claim 1, wherein the main body comprises external threading.
12. The distraction device of claim 1, wherein the main body comprises an external coating.
13. The distraction device of claim 1, wherein the base comprises an internal cavity configured to align with the internal duct of the main body during use, to form a contiguous channel.
14. The distraction device of claim 13, wherein the diameter of the opening into the cavity in the base is smaller than the diameter of the cavity.
15. The distraction device of claim 14, wherein an end of the elongated member is configured to be inside the cavity during use, and wherein the diameter of the end is larger than the diameter of the opening into the cavity.
16. The distraction device of claim 1, wherein the base has a proximal surface that is adjacent the main body in the undistracted position, and a distal surface, and wherein the base is tapered inwardly from the proximal to the distal surfaces.
17. The distraction device of claim 1, wherein the base slidably engages the main body, and wherein the base is inhibited from rotating with respect to the main body.
18. The distraction device of claim 1, wherein the main body comprises holes and the base comprises pins configured to engage the holes in the main body.
19. The distraction device of claim 1, wherein the main body comprises one or more grooves and the base comprises one or more finger projections configured to fit in the one or more grooves in the undistracted position.
20. The distraction device of claim 1, wherein a portion of the base telescopically engages the main body.
21. The distraction device of claim 1, wherein the base comprises external threading.
22. The distraction device of claim 1, wherein the base comprises an external coating.
23. The distraction device of claim 1, wherein the activation device is a hexagonal head, a square head, a polygonal cavity, a square cavity, a slot, or a crossed slot.
24. The distraction device of claim 1, wherein the activation device is a square cavity.
25. The distraction device of claim 1, wherein the elongated member is from about 3 millimeters to about 20 millimeters in length.
26. The distraction device of claim 1, further comprising a dental abutment attached to the device.

27. A dental distraction device comprising a main body, a base, and an elongated member, wherein:
   the main body defines a concentric axial channel with internal threading;
   the elongated member comprises complementary threading such that when the two sets of threads are engaged, rotation of the elongated member with respect to the main body urges the main body to threadably advance along the elongated member;
   the base defines a closed ended support for an end of the elongated member, against which the elongated member is freely rotatable; and
   the device is configured to provide an attachment to a dental abutment.

28. The distraction device of claim 27, wherein the distraction device provides a connection for an abutment requiring an external hexagonal attachment, an 8° Morse taper configuration, a spline configuration, an internal hexagon, a screw retained abutment, a cement retained abutment, an exterior square post, an exterior octagonal post, an internal square, or an internal octagon.

29. The distraction device of claim 27, wherein the top of the main body comprises a connector for driving the distraction device into a bone.

30. The distraction device of claim 27, wherein the main body comprises external threading.

31. The distraction device of claim 27, wherein the base slidably engages the main body, and wherein the base is inhibited from rotating with respect to the main body.

32. The distraction device of claim 27, wherein the main body comprises holes and the base comprises pins configured to engage the holes in the main body.

33. The distraction device of claim 27, wherein the main body comprises one or more grooves and the base comprises one or more finger projections configured to fit in the one or more grooves in the undistracted position.

34. The distraction device of claim 27, wherein a portion of the base telescopically engages the main body.

35. The distraction device of claim 27, further comprising a dental abutment or prosthesis attached to the main body.

36. A distraction device comprising:
   an elongate main body, wherein the main body comprises:
      a threaded internal duct; and
      a top configured to connect to a dental abutment;
   a base comprising an internal cavity, wherein the internal cavity is configured to align with the internal duct of the main body during use, to form a contiguous channel to the top of the main body, and wherein the cavity terminates in a surface configured to accept an end of an elongated member and provide a solid distraction platform against which an elongated member is freely rotatable; and
   an elongated member comprising external threading configured to mate with the internal threading of the main body and wherein the elongated member is configured to be disposed within the internal duct of the main body and extend into the cavity of the base;
   wherein upon engaging the threads and rotating the elongated member with respect to the main body, the elongated member is driven through the duct of the main body toward the base.

37. The distraction device of claim 36, wherein the top of the main body comprises a male connector for an abutment.

38. The distraction device of claim 36, wherein the top of the main body comprises a female connector for an abutment.

39. The distraction device of claim 36, wherein the distraction device provides a connection for an abutment requiring an external hexagonal attachment, an 8° Morse taper configuration, a spline configuration, an internal hexagon, a screw retained abutment, a cement retained abutment, an exterior square post, an exterior octagonal post, an internal square, or an internal octagon.

40. The distraction device of claim 36, wherein the top of the main body comprises a connector for driving the distraction device into a bone.

41. The distraction device of claim 36, wherein the base slidably engages the main body, and wherein the base is inhibited from rotating with respect to the main body.

42. The distraction device of claim 36, wherein the main body comprises holes and the base comprises pins configured to engage the holes in the main body.

43. The distraction device of claim 36, wherein the main body comprises one or more grooves and the base comprises one or more finger projections configured to fit in the one or more grooves in the undistracted position.

44. The distraction device of claim 36, wherein a portion of the base telescopically engages the main body.

45. The distraction device of claim 36, further comprising a dental abutment or prosthesis attached to the main body.

46. The distraction device of claim 36, wherein the elongated member comprises a hexagonal head, a square head, a polygonal cavity, a square cavity, a slot, or a crossed slot configured to activate the elongated member.

47. A distraction device comprising:
   an elongate main body, wherein the main body comprises:
      a threaded internal duct; and
      a top comprising an external hex connector for an abutment;
   a base comprising an internal cavity, wherein the internal cavity is configured to align with the internal duct of the main body during use, to form a contiguous channel to the top of the main body, and wherein the cavity terminates in a surface configured to accept an end of an elongated member and provide a solid distraction platform against which an elongated member is freely rotatable; and
   an elongated member comprising external threading configured to mate with the internal threading of the main body and wherein the elongated member is configured to be disposed within the internal duct of the main body and extend into the cavity of the base;
   wherein upon engaging the threads and rotating the elongated member with respect to the main body, the elongated member is driven through the duct of the main body toward the base.

48. The distraction device of claim 47, wherein the main body comprises external threading.

49. The distraction device of claim 47, wherein the elongated member comprises a square cavity for turning the elongated member.

50. The distraction device of claim 47, wherein the base slidably engages the main body, and wherein the base is inhibited from rotating with respect to the main body.

51. The distraction device of claim 47, wherein the main body comprises holes and the base comprises pins configured to engage the holes in the main body.

52. The distraction device of claim 47, wherein the main body comprises one or more grooves and the base comprises one or more finger projections configured to fit in the one or more grooves in the undistracted position.

53. The distraction device of claim 47, wherein a portion of the base telescopically engages the main body.

54. A distraction device comprising:
   an elongate main body, wherein the main body comprises:
      a threaded internal duct;
      a top comprising an 8° taper configuration for connection to an abutment; and
      a connection configured to engage a driver to drive the device into a bone;
   a base comprising an internal cavity, wherein the internal cavity is configured to align with the internal duct of the main body during use, to form a contiguous channel to the top of the main body, and wherein the cavity terminates in a surface configured to accept an end of an elongated member and provide a solid distraction platform against which an elongated member is freely rotatable; and
   an elongated member comprising external threading configured to mate with the internal threading of the main body and wherein the elongated member is configured to be disposed within the internal duct of the main body and extend into the cavity of the base;
   wherein upon engaging the threads and rotating the elongated member with respect to the main body, the elongated member is driven through the duct of the main body toward the base.

55. The distraction device of claim 54, wherein the connection configured to engage a driver comprises an internal hexagon.

56. The distraction device of claim 54, wherein the connection configured to engage a driver comprises one or more slots.

57. The distraction device of claim 54, wherein the main body comprises external threading.

58. The distraction device of claim 54, wherein the elongated member comprises a polygonal cavity for turning the elongated member.

59. The distraction device of claim 54, further comprising a dental abutment attached to the main body.

60. The distraction device of claim 54, wherein the base slidably engages the main body, and wherein the base is inhibited from rotating with respect to the main body.

61. The distraction device of claim 54, wherein the main body comprises holes and the base comprises pins configured to engage the holes in the main body.

62. The distraction device of claim 54, wherein the main body comprises one or more grooves and the base comprises one or more finger projections configured to fit in the one or more grooves in the undistracted position.

63. The distraction device of claim 54, wherein a portion of the base telescopically engages the main body.

64. A distraction device comprising:
   a main body, wherein the main body comprises:
      a threaded internal duct;
      a top configured to provide a connector for an abutment; and
      a bottom surface comprising one or more holes extending into the main body;
   a base configured to provide a solid distraction platform against which an elongated member is freely rotatable and comprising one or more pins on the surface configured to engage the one or more holes in the bottom surface of the main body during use; and
   an elongated member comprising external threading configured to mate with the internal threading of the main body and wherein the elongated member is configured to be disposed within the internal duct of the main body and contact the base;
   wherein upon engaging the threads and rotating the elongated member with respect to the main body, the elongated member is driven through the duct of the main body toward the base.

65. The distraction device of claim 64, wherein the main body comprises external threading configured to be screwed into a predrilled hole in a bone.

66. The distraction device of claim 64, wherein the elongated member comprises a square cavity in the top thereof, configured to provide a connection for a square headed wrench or driver.

67. The distraction device of claim 64, wherein the distraction device provides a connection for an abutment requiring an external hexagonal attachment, an 8° Morse taper configuration, a spline configuration, an internal hexagon, a screw retained abutment, a cement retained abutment, an exterior square post, an exterior octagonal post, an internal square, or an internal octagon.

68. The distraction device of claim 64, wherein the main body comprises a connector configured to drive the device into a bone.

69. The distraction device of claim 64, further comprising a dental abutment attached to the main body.

70. A distraction device comprising:
   a substantially cylindrical main body, wherein the main body comprises:
      a threaded internal duct;
      a top configured to provide a connector for an abutment; and
      one or more grooves on the exterior surface;
   a base configured to provide a solid distraction platform against which an elongated member is freely rotatable and comprising one or more fingers configured to engage the one or more grooves on the surface of the main body during use; and
   an elongated member comprising external threading configured to mate with the internal threading of the main body and wherein the elongated member is configured to be disposed within the internal duct of the main body and contact the base;
   wherein upon engaging the threads and rotating the elongated member with respect to the main body, the elongated member is driven through the duct of the main body toward the base.

71. The distraction device of claim 70, wherein the elongated member comprises a square cavity in the top thereof, configured to provide a connection for a square headed wrench or driver.

72. The distraction device of claim 70, wherein the main body comprises a connector configured to drive the device into a bone.

73. The distraction device of claim 70, wherein the distraction device provides a connection for an abutment requiring an external hexagonal attachment, an 8° Morse taper configuration, a spline configuration, an internal hexagon, a screw retained abutment, a cement retained abutment, an exterior square post, an exterior octagonal post, an internal square, or an internal octagon.

74. The distraction device of claim 70, further comprising a dental abutment attached to the main body.

75. A distraction device comprising:
   a main body, wherein the main body comprises:
      a threaded internal duct; and
      a top configured to provide a connector for an abutment;
   a base configured to provide a solid distraction platform against which an elongated member is freely rotatable and configured to telescopically engage the main body during use; and an elongated member comprising external threading configured to mate with the internal threading of the main body and wherein the elongated member is configured to be disposed within the internal duct of the main body and contact the base;

wherein upon engaging the threads and rotating the elongated member with respect to the main body, the elongated member is driven through the duct of the main body toward the base.

76. The distraction device of claim 75, wherein the main body comprises external threading configured to be screwed into a predrilled hole in a bone.

77. The distraction device of claim 75, wherein the elongated member comprises a square cavity in the top thereof, configured to provide a connection for a square headed wrench or driver.

78. The distraction device of claim 75, wherein the distraction device provides a connection for an abutment requiring an external hexagonal attachment, an 8° Morse taper configuration, a spline configuration, an internal hexagon, a screw retained abutment, a cement retained abutment, an exterior square post, an exterior octagonal post, an internal square, or an internal octagon.

79. The distraction device of claim 75, wherein the main body comprises a connector configured to drive the device into a bone.

80. The distraction device of claim 75, further comprising a dental abutment attached to the main body.

81. A method of providing a dental implant in an area of bone deficiency, comprising:
   providing a bone distraction device, the device comprising:
      (a) an elongate main body, wherein the main body comprises:
         an internal duct; and
         a top configured to connect to a dental abutment;
      (b) a base configured to accept an end of an elongated member and provide a distraction platform; and
      (c) an elongated member comprising an activation device and configured to be disposed within the internal duct of the main body and contact the base;
      wherein activation is effective to urge the elongated member through the channel of the main body and against the base, to cause separation of the main body and the base;
   drilling a hole in the bone, wherein the hole is of a size and shape to accommodate the bone distraction device;
   making an osteotomy just below the hole;
   inserting the bone distraction device in the hole;
   separating the superior bone segments and inferior bone segments;
   separating the main body and the base by activating the elongated member, thus further separating the superior and inferior bone segments;
   allowing the bone callus between the bone segments to grow;
   repeating the two previous steps until the desired bone height is reached; and
   allowing the bone distraction device to remain in the distracted bone to serve as a dental implant.

82. A method of manufacturing a combination bone distraction and dental implant device, the method comprising:
   providing a main body, wherein the main body comprises:
      an internal channel; and
      a top designed to accommodate a dental abutment;
   providing a base configured to accept an end of an elongated member and provide a solid distraction platform against which an elongated member is freely rotatable;
   providing an elongated member configured to be disposed within and extending into the internal channel of the main body and contacting the base; the elongated member further defined as comprising:
      an activation device, wherein activation is effective to move the main body along the elongated member, to cause separation of the main body and the base.

83. A method of anchoring a dental prosthesis in an area of low bone density comprising:
   providing a bone distraction device, the device comprising:
      (a) a main body, wherein the main body comprises:
         a threaded internal channel;
         external threads; and
         a top designed to accommodate a dental abutment;
      (b) a base configured to accept an end of an elongated member and provide a solid distraction platform against which an elongated member is freely rotatable;
      (c) an elongated member disposed within and extending into the internal channel of the main body and contacting the base; the elongated member further defined as comprising:
         threads configured to mate with the threaded internal channel of the main body; and
         an activation device, wherein activation is effective to engage the threads on the elongated member with the threads on the internal channel of the main body and upon rotation of the elongated member, to cause separation of the main body and the base;
   making an incision in the gum tissue and exposing the bone of the upper or lower jaw;
   drilling a hole the diameter of the device;
   making an osteotomy in the jaw bone just below the hole;
   tapping the bone to accommodate external threads on the main body;
   screwing the device into position;
   separating the superior osteotomized bone segments and inferior osteotomized bone segments;
   closing the gingiva;
   turning the shaft by means of an activation wrench;
   repeating the previous step until the desired bone height is achieved; and
   attaching a dental abutment to the device.

* * * * *